United States Patent
Cho et al.

(10) Patent No.: US 8,131,492 B2
(45) Date of Patent: Mar. 6, 2012

(54) METHOD OF EVALUATING A FILM

(75) Inventors: Shien Cho, Kanagawa (JP); Markus Wilde, Tokyo (JP); Katsuyuki Fukutani, Tokyo (JP)

(73) Assignees: Renesas Electronics Corporation, Kanagawa (JP); The Foundation for the Promotion of Industrial Science, Tokyo (JP)

( * ) Notice: Subject to any disclaimer, the term of this patent is extended or adjusted under 35 U.S.C. 154(b) by 491 days.

(21) Appl. No.: 11/964,206

(22) Filed: Dec. 26, 2007

(65) Prior Publication Data

US 2008/0183420 A1 Jul. 31, 2008

(30) Foreign Application Priority Data

Dec. 25, 2006 (JP) ................................ 2006-348095

(51) Int. Cl.
*G01N 37/00* (2006.01)
*G01D 3/00* (2006.01)
(52) U.S. Cl. ........... 702/81; 702/109; 702/110; 702/111
(58) Field of Classification Search ............. 702/81–83, 702/109–112; 438/14, 18
See application file for complete search history.

(56) References Cited

U.S. PATENT DOCUMENTS

| | | | | |
|---|---|---|---|---|
| 4,907,064 A | * | 3/1990 | Yamazaki et al. | 257/649 |
| 5,825,068 A | * | 10/1998 | Yang | 257/380 |
| 2003/0001177 A1 | * | 1/2003 | Okutoh et al. | 257/295 |
| 2004/0058555 A1 | * | 3/2004 | Moriceau et al. | 438/736 |
| 2009/0127137 A1 | * | 5/2009 | Golz et al. | 206/7 |
| 2010/0119728 A1 | * | 5/2010 | Johnson et al. | 427/535 |

OTHER PUBLICATIONS

Michael A. Briere et al., "A Quantitative Investigation of Hydrogen in the Metal-Oxide-Silicon System Using NRA", IEEE Transactions on Nuclear Science, vol. 37, No. 6, Dec. 1990, pp. 1-12.

Susumu Shuto et al., "Impact of Passivation Film Deposition and Post-Annealing on the Reliability of Flash Memories", 1997, IEEE, pp. 1-8.

JP Office Action dated Nov. 8, 2011, with English Translation.

M.A. Briere, ETC., "A Quantitative Investigation of Hydrogen in the Metal-Oxide-Silicon System Using NRA", IEEE Transactions on Nuclear Science, vol. 37, No. 6, Dec. 1990, pp. 1658-1669.

K.H. Ecker, ETC., "Nuclear reaction analysis of hydrogen migration in silicon dioxide films on silicon under 15N ion irradiation", Nuclear Instruments and Methods in Physics Research B, vols. 161-163, 2000, pp. 682-685.

\* cited by examiner

*Primary Examiner* — Phuong Huynh
(74) *Attorney, Agent, or Firm* — Young & Thompson

(57) ABSTRACT

A method of directly measuring hydrogen permeability of a film is provided. The method of evaluating a film includes acquiring, with respect to a specimen including a plurality of films stacked on each other, ion dose-dependence data of intensity of γ-beam generated by hydrogen resonant nuclear reaction, and fitting the data with a functional equation of the ion dose.

13 Claims, 9 Drawing Sheets

$$I(N) = H_0 + A*[1-\exp(\sigma*N)]$$

METHOD OF EVALUATING A FILM

This application is based on Japanese patent application No. 2006-348095, the content of which is incorporated hereinto by reference.

BACKGROUND

1. Technical Field

The present invention relates to a method of evaluating a film, and more particularly to a method of evaluating diffusion behavior of hydrogen in the film.

2. Related Art

For a thin film, permeability with respect to hydrogen-related species (H, $H_2$, OH, $H_2O$) is a critical property. In this relation, differential-pressure gas chromatography may be employed to measure the permeability of hydrogen gas or vapor. However, no method has so far been developed for measuring a hydrogen diffusion cross section of an ultra-thin film of a nanometer order such as those in an LSI, especially under a state where the specimen is stacked on a substrate. Based on Resonant nuclear reaction analysis (hereinafter, NRA), which is a process of resolving the depth of the specimen to thereby measure the quantity of hydrogen, for example the non-patented document 1 reports a phenomenon that an NRA signal in a $SiO_2$/Si interface changes depending on primary ion dose.

[Non-patented document 1] Michael A. Briere et al., "A QUANTITATIVE INVESTIGATION OF HYDROGEN IN THE METAL-OXIDE-SILICON SYSTEM USING NRA", IEEE TRANSACTIONS ON NUCLEAR SCIENCE, VOL. 37, NO. 6, DECEMBER 1990, pp. 1658-1669

[Non-patented document 2] Susumu Shuto et al., "Impact of passivation film deposition and post-annealing on the reliability of flash memories", IEEE Proceeding of IRPS 1997, pp. 17-24

The present inventors have recognized as follows. It is known in the semiconductor field that hydrogen imposes a great impact on the reliability of a MOS transistor or the like, and hence a method that provides the hydrogen permeability of the thin film, including an interlayer dielectric film, has been eagerly sought for. Methods of measuring the quantity of hydrogen, however, are limited and practically effective measuring methods have barely been developed. Accordingly, theoretical calculation has usually been the only recourse in estimating the quantity of hydrogen. In this respect, correlation between the refractive index of the film and the hydrogen permeability has recently been focused on, however a theoretically corroborated correlation has not yet been established. Therefore, it is of primary importance to establish a method of directly measuring the hydrogen permeability and other associated properties of the film (for example, refer to the non-patented document 2).

SUMMARY

In one aspect of the present invention, there is provided a method of evaluating a film, comprising acquiring, with respect to a specimen including a plurality of films stacked on each other, ion dose-dependence data of intensity of γ-beam generated by hydrogen resonant nuclear reaction; and fitting the data with a functional equation of the ion dose.

By the method thus arranged, primary ion of the NRA which has an extremely small reaction cross section (for example, approximately $10^{-24}$ $cm^2$) excites a large number of secondary electrons. The secondary electrons cause the hydrogen bond in the film to be disconnected, thus creating a free hydrogen that is capable of diffusing. The free hydrogen diffuses into a region where trap density is high, to be thereby redistributed. The NRA is capable of moving hydrogen through the secondary electrons and measuring the hydrogen concentration at a time. The present invention enables analyzing the redistribution process of hydrogen, to thereby measure the hydrogen permeability of the film, which serves as a reservoir of hydrogen, and measure the hydrogen trap density of the film that accepts hydrogen, at a time. More specifically, the hydrogen permeability of the film that supplies hydrogen can be obtained based on the constant that reflects the change rate of the γ-beam, among the constants in the functional equation employed for the fitting. Also, the hydrogen trap density at a position where the nuclear reaction takes place can be obtained, based on the saturation value of the γ-beam.

Thus, the present invention provides a method of evaluating a film that enables directly measuring hydrogen permeability of the film and other associated properties.

BRIEF DESCRIPTION OF THE DRAWINGS

The above and other objects, advantages and features of the present invention will be more apparent from the following description of certain preferred embodiments taken in conjunction with the accompanying drawings, in which.

DETAILED DESCRIPTION OF PREFERRED EMBODIMENTS

The invention will be now described herein with reference to illustrative embodiments. Those skilled in the art will recognize that many alternative embodiments can be accomplished using the teachings of the present invention and that the invention is not limited to the embodiments illustrated for explanatory purposes.

Hereunder, an exemplary embodiment of a method of evaluating a film according to the present invention will be described in details, referring to the accompanying drawings. In all the drawings, same constituents are given the same numeral, and the description thereof will not be repeated.

Generally, the evaluating method includes acquiring, with respect to a specimen including a plurality of films stacked on each other, ion dose-dependence data of intensity of γ-beam generated by hydrogen resonant nuclear reaction, and fitting the data with a functional equation of the ion dose.

Figure 1A:
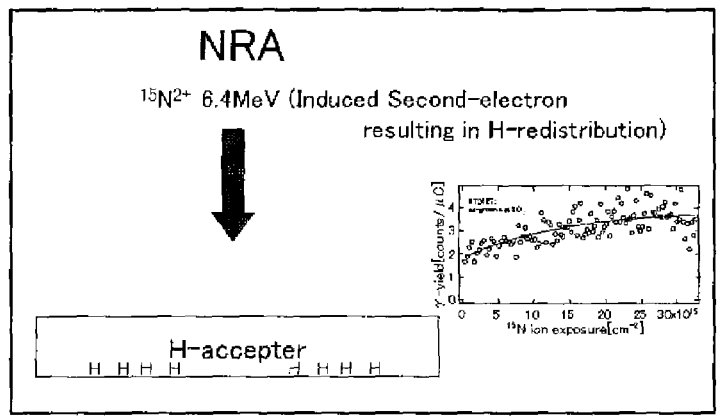
FIGS. 1A and 1B are diagrams for explaining a principle of a conventional method and a method according to an embodiment of the present invention, respectively.
Figure 1B:
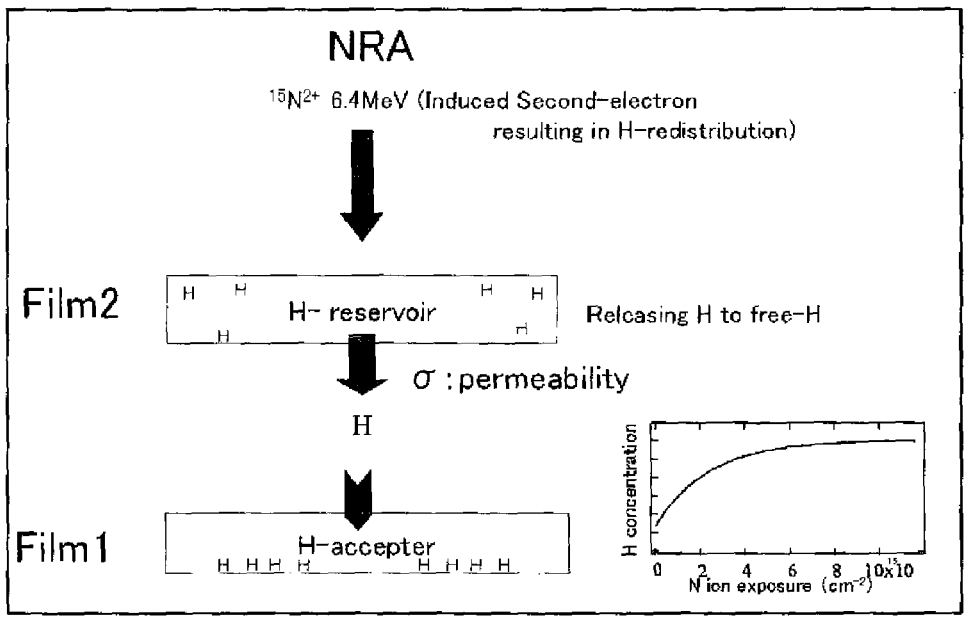

FIGS. 1A and 1B are diagrams for explaining principles of a conventional method and the method according to the embodiment of the present invention. A major disadvantage in the quantification of hydrogen by the conventional method is the phenomenon that hydrogen in the interface of a thin film gradually increases along with the ion dose. Besides, because the amount of free hydrogen in a monolayer film is small, the NRA signal does not reach a saturation point. Thus, the significance of saturation has not been focused on.

According to this embodiment, the primary ion of the NRA excites the secondary electrons upon passing through an upper layer containing hydrogen, and thereby creates free hydrogen. Since a lower layer contains a large number of hydrogen traps, hydrogen diffuses toward an interface between the lower layer containing many traps and a substrate. Because of the sufficient quantity of free hydrogen, the lower layer becomes saturated with hydrogen in the meantime. Accordingly, detecting the change in hydrogen concentration in the vicinity of the interface and the hydrogen saturation value enables measuring the hydrogen diffusion cross section of the upper layer and the trap density of the lower layer.

Figure 2:
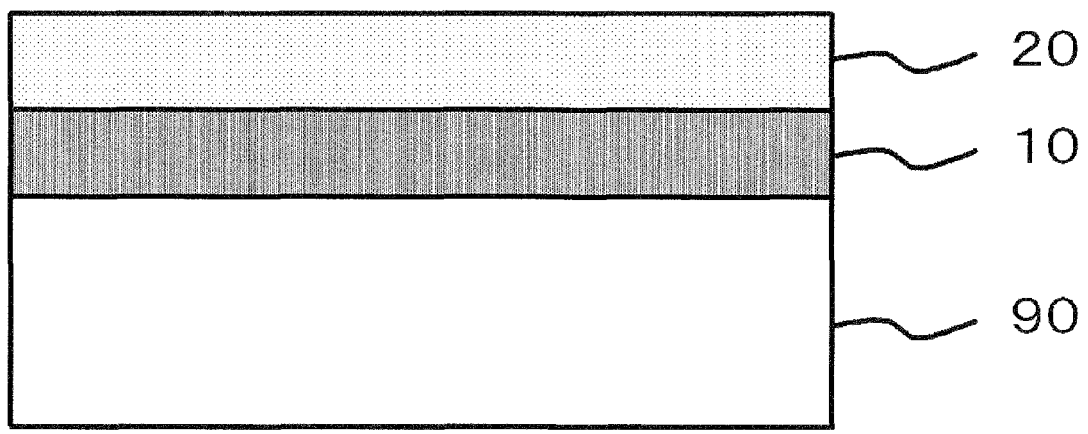
FIG. 2 is a cross-sectional view of a specimen employed in a embodiment of the present invention.

FIG. 2 is a cross-sectional view of a specimen employed in this embodiment. A thin film 20 (upper layer) which is to be examined for the hydrogen diffusion cross section is stacked on a thin film 10 (lower layer) which is to be examined for the hydrogen trap density. The thin film 10 contains a greater number of hydrogen traps than the thin film 20. The thin film 20 contains a large quantity of hydrogen and serves as a reservoir of hydrogen. The thin films 10, 20 constitute the specimen. The thickness of the specimen, in other words the sum of the thickness of the thin films 10, 20 may be, for example, equal to or more than 2 nm and equal to or less than 0.5 μm. The specimen is provided on a substrate 90. It is preferable that the substrate 90 has a lower hydrogen absorption than that of the respective thin films 10, 20. Suitable examples of the substrate include a monocrystalline silicon substrate.

In this embodiment, firstly a profile of the hydrogen concentration in the depth direction of the specimen (depth profile) is acquired, while changing the ion energy of the NRA. Based on the profile, hydrogen location before redistribution and hydrogen trap location after the redistribution can be detected. The NRA ion energy is then fixed at two peak positions in the profile, and data on the dependence of γ-beam intensity on the incident ion dose is acquired. Finally, the curve obtained through a minimum square method is fitted with an ion dose function. Such process leads to obtaining the hydrogen permeability of the thin film 20, the reservoir of hydrogen, based on a constant that reflects the change rate of the γ-beam, as well as the quantity of trapped hydrogen at the position where the nuclear reaction takes place, based on the saturation value of the γ-beam.

Thus, in this embodiment the resonant nuclear reaction measurement is performed with respect to hydrogen utilizing a resonant nuclear reaction apparatus, in the step of acquiring the data. The resonant nuclear reaction measurement includes the acquisition of the hydrogen concentration profile in the depth direction of the specimen, the identification of the peak positions of the hydrogen concentration based on the profile, and the acquisition of the dependence of the hydrogen concentration on ion dose at the peak position.

Hereunder, examples of the present invention will be described in details based on the drawings.

Example 1

The specimen shown in FIG. 2 was employed. In this example, a $SiO_2$ film of 25 nm in thickness was prepared as the thin film 10, and a SiN film of 10 nm in thickness as the thin film 20. A silicon substrate was prepared as the substrate 90. To prove that the hydrogen permeability can be measured according to the present invention, two types of SiN films were deposited on the same $SiO_2$ film, namely a SiN-1 film deposited by a plasma-CVD process, and a SiN-2 film deposited by a LP-CVD process.

Figure 3A:
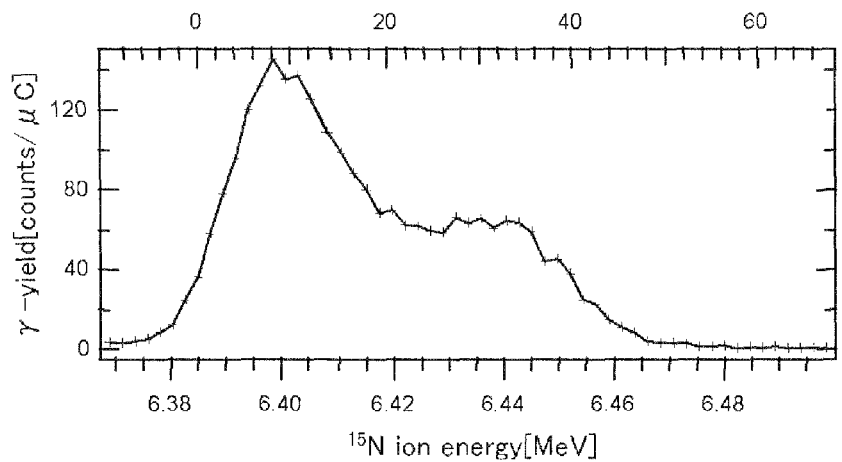
FIGS. 3A and 3B are graphs showing a hydrogen concentration profile in a depth direction of the specimen, with respect to a SiN-1 film and a SiN-2 film respectively.
Figure 3B:
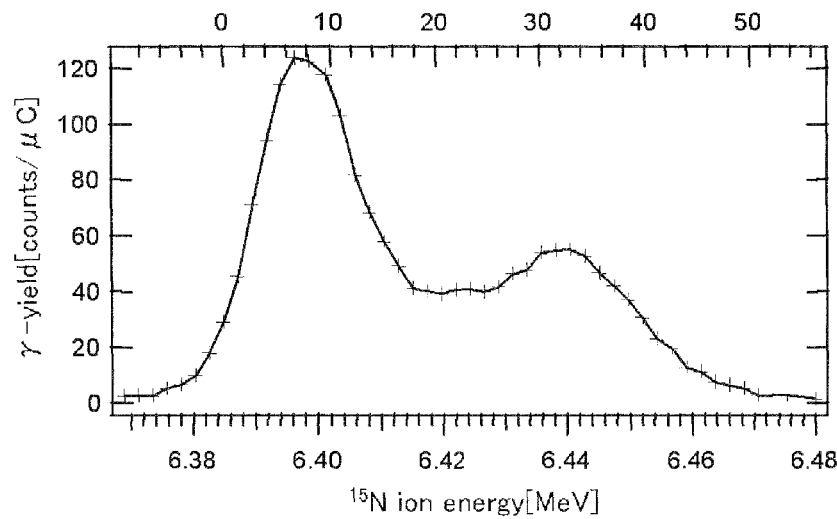

FIGS. 3A and 3B are graphs showing the hydrogen concentration profile in a depth direction of the specimen, with respect to the SiN-1 film and the SiN-2 film respectively. Two peaks were observed in the profiles. The relatively higher peak (on the left) is the peak in the SiN film. The relatively lower peak (on the right) is the peak in the $Sio_2$/Si interface. The primary ion energy of the NRA was fixed at the respective two peaks, and the ion dose-dependence of the peak intensity was measured.

Figure 4:
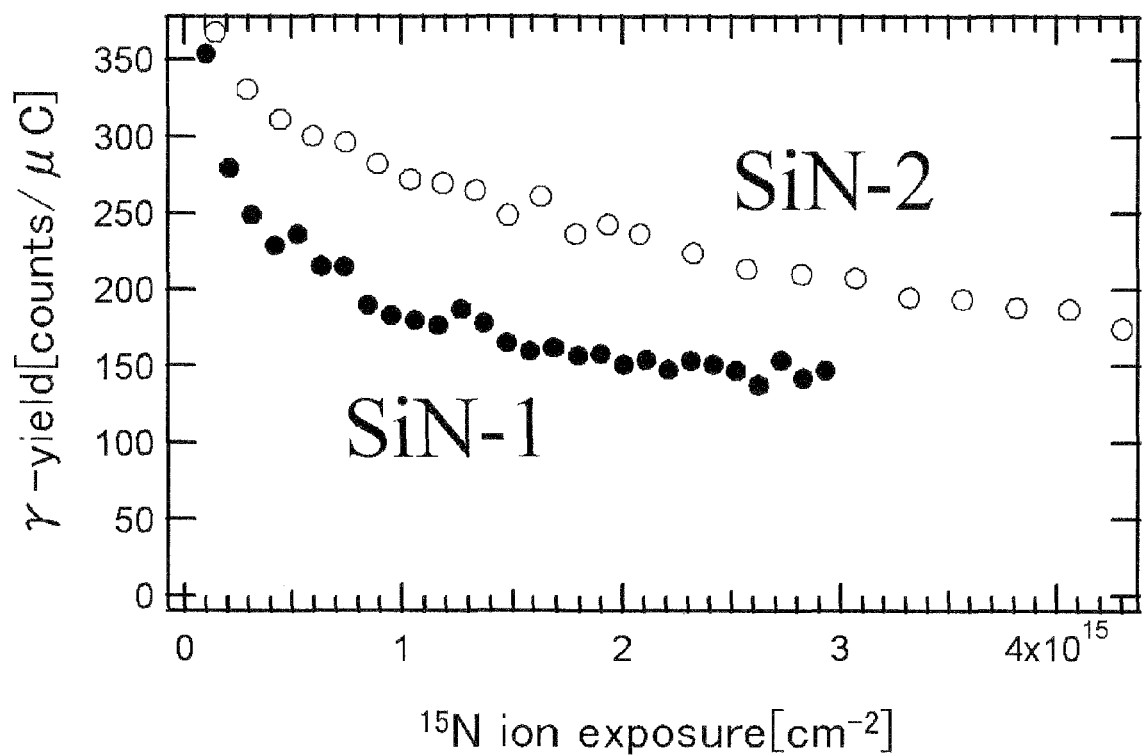
FIG. 4 is a graph showing ion dose-dependence of a peak in the SiN film.
Figure 5:
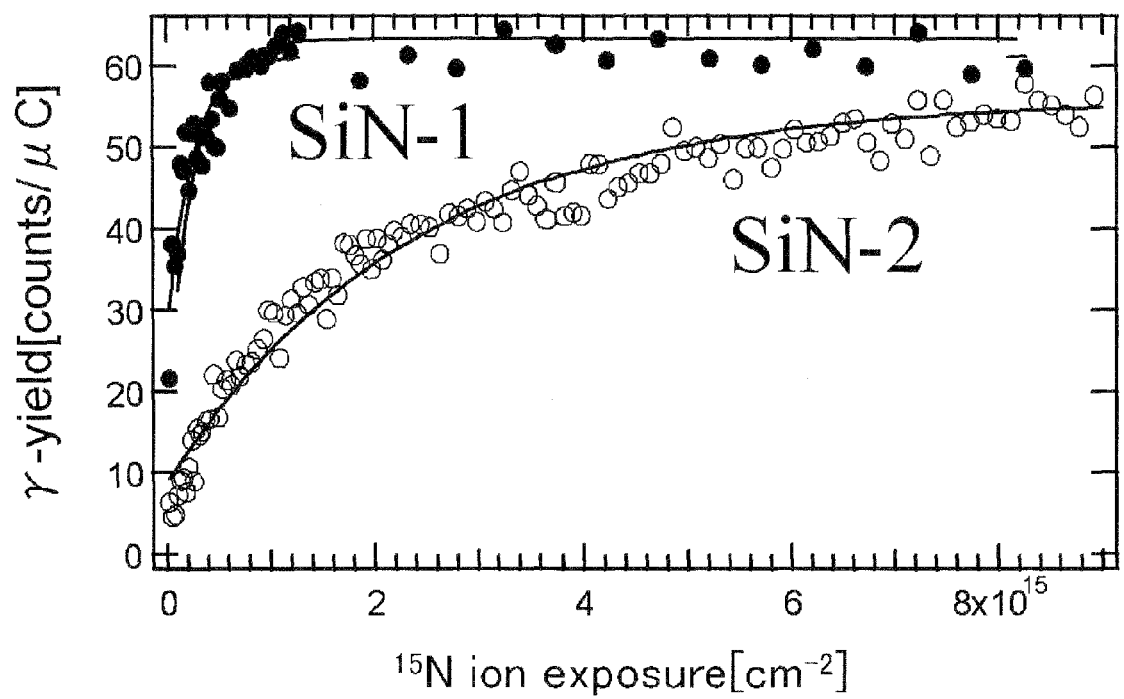
FIG. 5 is a graph showing ion dose-dependence of a peak in a $SiO_2$/Si interface.

FIG. 4 is a graph showing the ion dose-dependence of the peak in the SiN film. It is understood that, while the hydrogen concentration decreases because of the ion irradiation, the decrease rate is greater in the specimen with the SiN-1 film than in the specimen with the SiN-2 film. FIG. 5 is a graph showing the ion dose-dependence of the peak in the $SiO_2$/Si interface. It is understood that, while the quantity of hydrogen increases because of the ion irradiation, the increase rate apparently depends on the type of the SiN film. Thus, the specimen with the SiN-1 film reaches the saturation point quicker than the specimen with the SiN-2 film.

Figure 6:
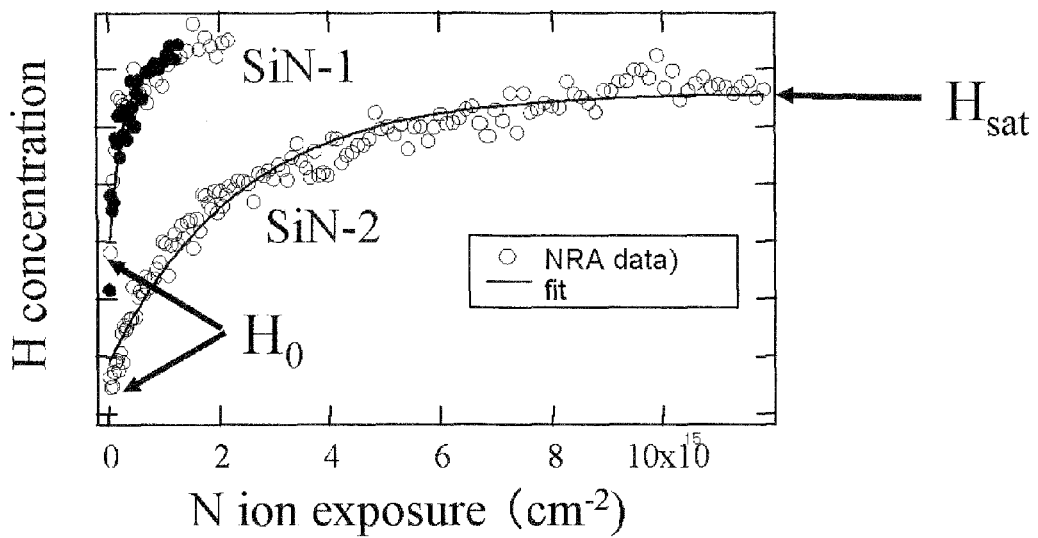
FIG. 6 is a graph for explaining the analysis result on the profile shown in FIG. 5.

FIG. 6 is a graph for explaining the analysis result on the profile shown in FIG. 5. As is apparent from FIG. 6, the curve representing the ion dose-dependence of the peak in the above interface can be properly fitted with the following equation (1). For the fitting, a method of least squares was employed.

$$I(N)=H_0+A\times\{1-\exp(-\sigma\times N)\} \tag{1}$$

In this equation, N represents the ion dose, $H_0$ the initial hydrogen concentration, and σ the hydrogen permeability of the upper layer (SiN film). When the saturation value of hydrogen is denoted by $H_{sat}$, $H_{sat}=H_0+A$ is satisfied. The $H_{sat}$ reflects the hydrogen trap density.

When the hydrogen permeability of the SiN-1 film and the SiN-2 film is denoted by σ1 and σ2 respectively, σ1/σ2 was nearly equal to 5. This means that the hydrogen permeability of the SiN-1 film is approximately five times as high as that of the SiN-2 film. It has also been confirmed that such result is well in accordance with the characteristic of a device.

Example 2

The specimen shown in FIG. 2 was employed. In this example also, a $SiO_2$ film of 25 nm in thickness was prepared as the thin film 10, and a SiN film of 10 nm in thickness as the thin film 20. In this case, to prove that the hydrogen trap density at a designated depth position in the thin film can be measured according to the present invention, two types of CVD oxide films were employed as the $SiO_2$ film, namely a $SiO_2$-1 film and a $SiO_2$-2 film. Both of the $SiO_2$ films were subjected to a post-anneal process after the CVD process. In the post-anneal process, the $SiO_2$-1 film was heated at 800° C., and the $SiO_2$-2 film was heated at 1000° C. As the SiN film, the above SiN-1 film was commonly used.

Figure 7A:
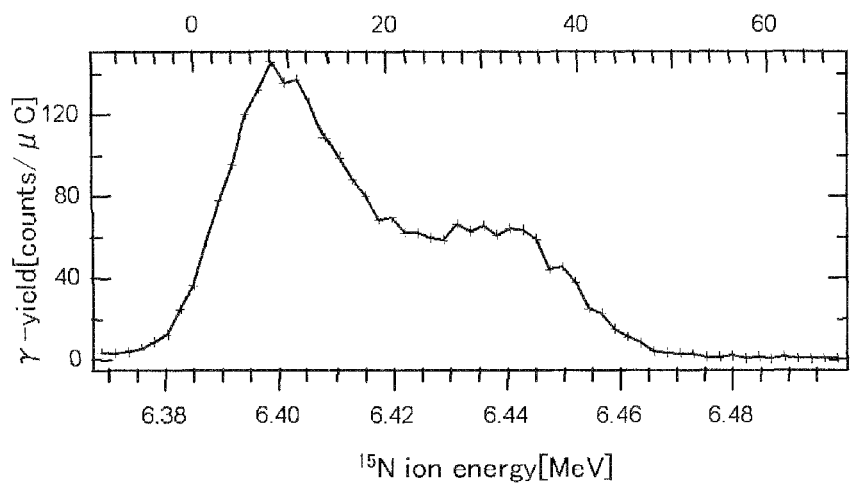
FIGS. 7A and 7B are graphs showing a hydrogen concentration profile in a depth direction of the specimen, with respect to a $SiO_2$-1 film and a $SiO_2$-2 film, respectively.
Figure 7B:
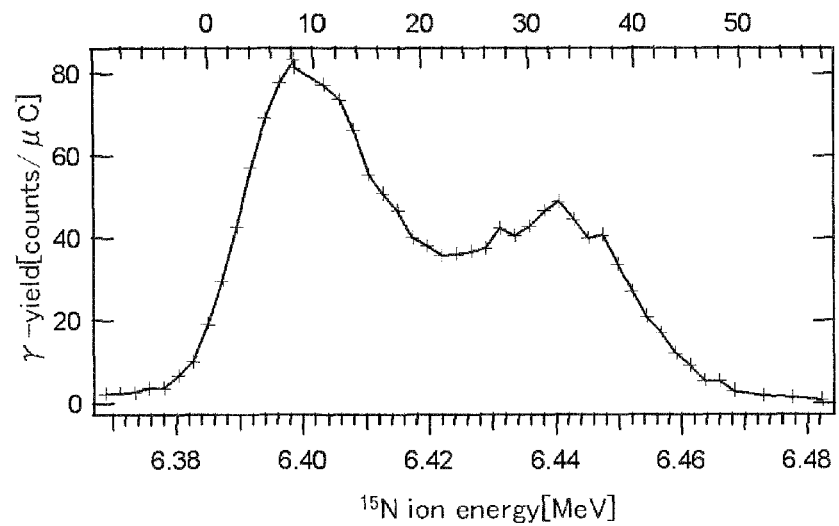

FIGS. 7A and 7B are graphs showing the hydrogen concentration profile in a depth direction of the specimen acquired through the NRA, with respect to the $SiO_2$-1 film and the $SiO_2$-2 film, respectively. As in example 1, a peak was observed each for the SiN film and for the $SiO_2$/Si interface.

Figure 8A:
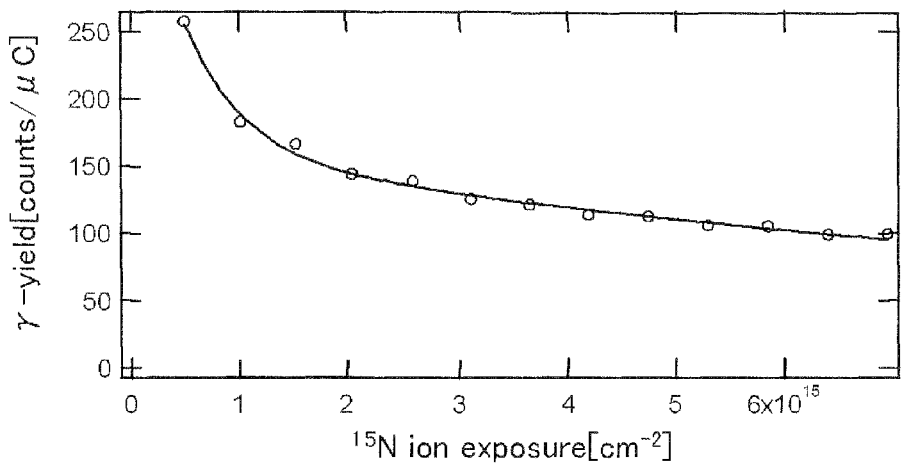
FIGS. 8A and 8B are graphs showing ion dose-dependence of a peak in SiN, with respect to the $SiO_2$-1 film and the $SiO_2$-2 film, respectively.
Figure 8B:
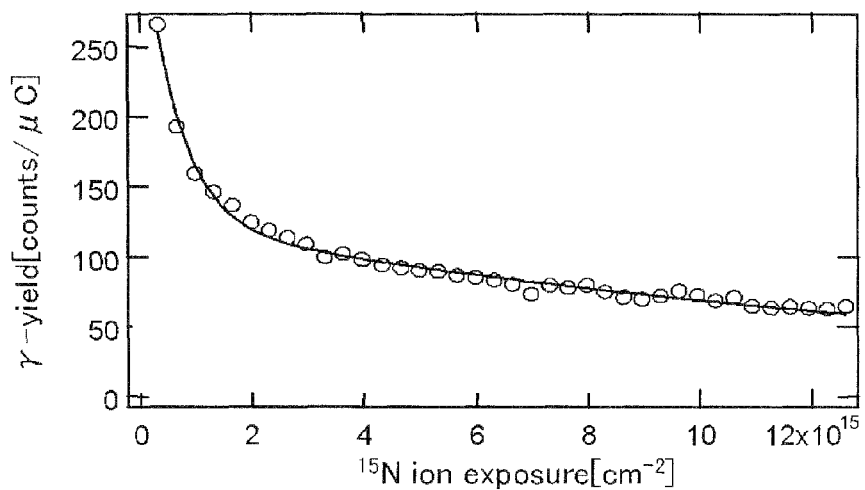

FIGS. 8A and 8B are graphs showing the ion dose-dependence of the peak in the SiN film, with respect to the $SiO_2$-1 film and the $SiO_2$-2 film, respectively. The graphs show the behavior of the hydrogen peak in the SiN film which decreases depending on the ion dose.

Figure 9:
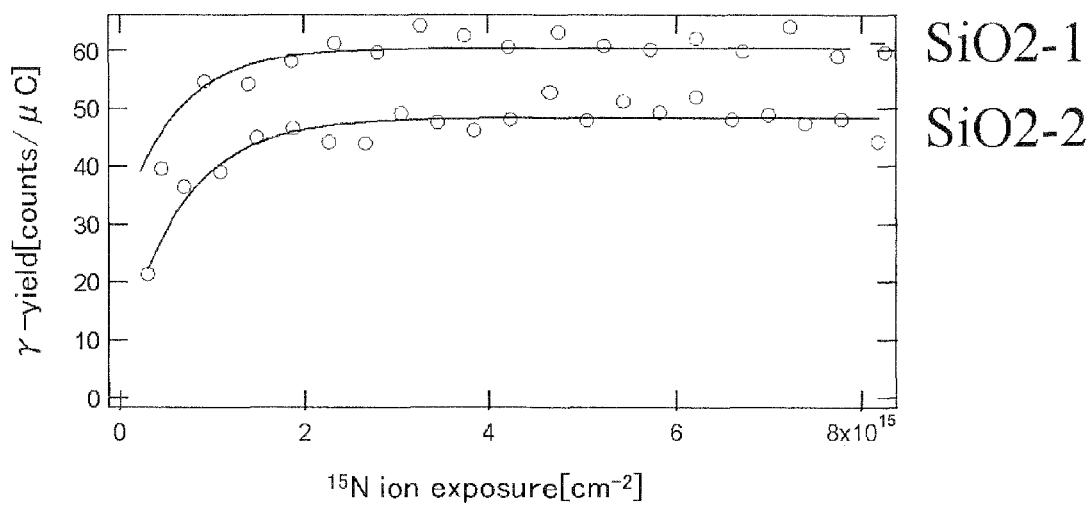
FIG. 9 is a graph showing ion dose-dependence of a peak in a $SiO_2$/Si interface.

FIG. 9 is a graph showing the ion dose-dependence of the peak in a $SiO_2$/Si interface. Although the curves start from different points because the initial hydrogen concentrations are different, their increase rates are almost the same. However, there was a major difference in the saturation level. The saturation level of the specimen with the $SiO_2$-2 film is approximately two thirds of that of the specimen with the $SiO_2$-1 film. It is believed that this originates from a difference in interface defect (hydrogen trap) due to the difference in post-anneal temperature.

The present invention is not limited to the foregoing embodiment, but may be modified in various manners. For example, the above step (acquiring the data and fitting the data) may be performed with respect to a plurality of specimens. This enables finding the difference in hydrogen permeability and in trap density among the films.

Also, the above step may be performed with respect to a plurality of depth positions in a specimen. Mapping the results in the depth directions leads to detecting the change in depth distribution of the trap and diffusion cross section in the depth direction. It is possible to evaluate the depth structural change of the film by detecting the change in depth.

Further, the above step may be performed under a plurality of specimen temperatures (the temperature of the above specimens) different from each other. Performing thus the measurement under different specimen temperatures enables finding the change by temperature in hydrogen permeability and hydrogen trap density of the thin film. In this case, it is preferable to change the specimen temperature in a range from a given negative temperature to the evaporation temperature of the specimen. In this case, further, the above step may be performed in a plurality of measurement atmospheres (type of gas, pressure) different from each other. This enables finding the change by temperature and atmosphere, in hydrogen permeability and hydrogen trap density of the thin film.

In addition, the above step may be performed with an electric field being applied to the specimen. This enables finding the behavior of the hydrogen permeability and the hydrogen trap density in the thin film subjected to the electric field.

It is apparent that the present invention is not limited to the above embodiment, and may be modified and changed without departing from the scope and spirit of the invention.

What is claimed is:

1. A method of measuring hydrogen permeability of a film, comprising:
    acquiring, with respect to a specimen including a plurality of films stacked on each other, a profile of hydrogen concentration in a stacking direction of said plurality of films by performing resonant nuclear reaction measurement with respect to hydrogen using a resonant nuclear reaction apparatus;
    acquiring ion dose-dependence data of intensity of γ-beam generated by hydrogen resonant nuclear reaction at peak positions of said profile;
    fitting said data with a functional equation of said ion dose; and
    determining hydrogen permeability of the film based on a constant that reflects a change rate of the γ-beam in the functional equation.

2. The method according to claim 1, wherein said acquiring said data and said fitting said data are performed with respect to a plurality of said specimen.

3. The method according to claim 1, wherein said acquiring said data and said fitting said data are performed with respect to a plurality of depth positions in said specimen.

4. The method according to claim 1, wherein said specimen has a thickness of equal to or more than 2 nm and equal to or less than 0.5 μm.

5. The method according to claim 1, wherein said specimen includes a layer that serves as a reservoir of hydrogen.

6. The method according to claim 1, wherein said specimen is provided on a substrate having a lower hydrogen absorption than that of said films constituting said specimen.

7. The method according to claim 6, wherein said substrate is a monocrystalline silicon substrate.

8. The method according to claim 1, wherein said plurality of films constituting said specimen include a first film and a second film containing a larger number of hydrogen traps than said first film.

9. The method according to claim 1, wherein said acquiring said data and said fitting said data are performed with respect to a plurality of specimen temperatures different from each other, in which a temperature of said specimen is defined as specimen temperature.

10. The method according to claim 9, wherein said specimen temperature in degree centigrade is changed in a range from a given negative temperature to an evaporation temperature of said specimen.

11. The method according to claim 9, wherein said acquiring said data and said fitting said data are performed in a plurality of measurement atmospheres different from each other.

12. The method according to claim 1, wherein said acquiring said data and said fitting said data are performed with an electric field being applied to said specimen.

13. A method of measuring hydrogen permeability of a film, comprising:
    acquiring, with respect to a specimen including a plurality of films stacked on each other, ion dose-dependence data of intensity of γ-beam generated by hydrogen resonant nuclear reaction using a resonant nuclear reaction apparatus;
    fitting said data with a functional equation of said ion dose; and
    determining hydrogen permeability of the film from the functional equation,
    wherein the functional equation is $$I(N)=H_0+A\times\{1-\exp(-\sigma\times N)\} \quad (1)$$

where N is the ion dose, $H_0$ is the initial hydrogen concentration, and σ is the hydrogen permeability, and
wherein the fitting step is a least squares fitting.

* * * * *